United States Patent [19]
Schneider et al.

[11] Patent Number: 5,549,546
[45] Date of Patent: Aug. 27, 1996

[54] INSUFFLATION DEVICE

[75] Inventors: Herbert Schneider, Mühlacker; Gunter Rentschler, Kraichtal–Münzesheim, both of Germany

[73] Assignee: Richard Wolf GmbH, Knittlingen, Germany

[21] Appl. No.: 377,439

[22] Filed: Jan. 24, 1995

[30] Foreign Application Priority Data

Jan. 28, 1994 [DE] Germany .......................... 44 02 467.3

[51] Int. Cl.⁶ .................................................. A61M 37/00
[52] U.S. Cl. .................................................. 604/26; 604/23
[58] Field of Search ................................ 604/26, 23, 24, 604/30; 128/747

[56] References Cited

U.S. PATENT DOCUMENTS

| | | | |
|---|---|---|---|
| 5,246,419 | 9/1993 | Absten | 128/747 |
| 5,292,304 | 3/1994 | Mantell et al. | 604/23 |
| 5,328,458 | 4/1994 | Sekino et al. | 604/23 |
| 5,423,741 | 6/1995 | Frank | 604/23 |

FOREIGN PATENT DOCUMENTS

| | | |
|---|---|---|
| 3611018 | 6/1987 | European Pat. Off. . |
| 0384155 | 8/1990 | European Pat. Off. . |
| 0517190 | 12/1992 | European Pat. Off. . |
| 2326734 | 4/1977 | France . |
| 3739003 | 5/1989 | Germany . |
| 3922746 | 8/1990 | Germany . |
| 2271427 | 4/1994 | United Kingdom . |

*Primary Examiner*—Randall L. Green
*Assistant Examiner*—Perry E. Van Over
*Attorney, Agent, or Firm*—Cohen, Pontani, Lieberman, Pavane

[57] ABSTRACT

A medical insufflation device having a control device with feedback sensors for regulating the flow of a gas into an inflatable body cavity. The device includes a conduit for channeling gas from a gas supply into an insufflation instrument, sensors for measuring gas pressure and gas flow in the conduit, and a control device responsive to the sensors for automatically regulating the pressure and flow of the gas into the body cavity from the conduit. The control device has an automatic processing unit for receiving the measured gas pressure and flow values from the sensors and for using those values to control an actuator in the conduit and which is operatively adjustable for regulating the flow of gas into the body cavity. During insufflation, when the pressure sensor detects a drop in pressure or that the measured pressure is no longer increasing, the control device automatically operates the actuator to reduce the pressure in the conduit until the gas flow falls to a minimum value such, for example, as zero while the body cavity remains open.

12 Claims, 3 Drawing Sheets

INSUFFLATION DEVICE

BACKGROUND OF THE INVENTION

1. Field of the Invention

The present invention relates to insufflation devices and, in particular, to a medical insufflation device having an automatic control device with feedback sensors for regulating and controlling the flow of gas into an inflatable body cavity.

2. Description of the Prior Art

Typically, prior to hysteroscopy, an insufflation device is employed to expand the cavum uteri with a gas through a probe or an endoscope channel. As the cavum uteri opens, a desired intrauterine pressure is established. Under normal anatomical circumstances, the insufflation pressure should preferably lie between approximately $0.5 \times 10^4$ and $1.0 \times 10^4$ Pa, and the gas flow (or mass flow) should preferably be between about 30 to 40 ml/min. Of course, a given maximum intra-uterine gas pressure should not be exceeded for medical reasons.

During a simulated operation, and prior to an actual examination, an operator checks or obtains permissible maximum values such, for example, as a maximum intra-uterine pressure value for the patient. It has been found that the maximum permissible insufflation pressure is in the range of approximately $1.99 \times 10^4$ to $2.66 \times 10^4$ Pa and the maximum gas flow should not exceed about 100 ml/min or, preferably, about 70 ml/min.

When a hysteroscope is moved back and forth during an examination, the intra-uterine pressure may change. However, after a short time a steady state or equilibrium pressure is re-established by the insufflation device. Naturally, the more the pressure in the body cavity rises, the smaller the quantity of gas flowing into the cavum uteri. When the pressure between the insufflation device and the cavum uteri reaches equilibrium, the flow of gas stops. With tubes closed, the intra-uterine pressure will rise to a pre-established level while the gas flow falls to zero.

In a normal operation (i.e. without automatic operation), and after the initial check for permissible maximum values, the operator manually monitors the maintenance of the maximum pressure and flow values, and constantly checking the displays of an insufflation device. When a hysteroscope is moved back and forth during examination, the insufflation pressure in the cavum uteri may change due to gas leakage through the scope itself, and/or through any other passages associated with the uterus being operated on. In response, the operator is required to make appropriate adjustments to the valves of the insufflation device so as to compensate for such pressure drops.

In order to relieve the operator (such, for example, as the examining physician) from having to perform these distracting mechanical tasks including instrument readings and the like, it is desirable that these tasks be performed automatically. In particular, it is desirable to have an insufflation device which automatically monitors and maintains intra-uterine pressure and gas flow at predetermined maximum values by automatically performing appropriate valve adjustments during examination.

German publication DE-C-39 22 746 discloses an insufflation device which comprises a gas suction circuit having an automatic shut-off. Tile suction circuit includes a pump whose suction side is connected to a flow output meter and a pressure transducer, and whose pressure side is connected to an endoscope. Measurement data from the pressure transducer and flow output meter are communicated to an electronic evaluation system for processing so that if any disturbance is detected in the suction circuit, the pump is automatically shut off. The device of the German publication, however, does not automatically monitor and maintain reduced pressure in an inflatable body cavity during insufflation.

SUMMARY OF THE INVENTION

It is accordingly an object of the present invention to provide an insufflation apparatus with a control device having an automatic processing unit which enables hysteroscopy to be carried out at significantly lower gas pressure and flow than has heretofore been required, and yet achieves sufficient opening of the body cavity to permit the ready conduct of such operations.

Another object of the present invention is to provide a control device having an automatic processing unit for use with an insufflation device so that during automatic operation of the insufflation device and, in particular, during the insufflation phase, a pressure sensor that either detects a drop in pressure or recognizes that the registered or measured pressure is no longer increasing, i.e., remains constant, causes an automatic processing unit to reduce the pressure or gas flow until the measured gas flow decreases to zero.

Of course, the gas flow and pressure values at which the pressure begins to drop or from which it does not continue to rise may be different than the aforementioned maximum values. Also, at least in theory, the control characteristics of the insufflation device are the same during normal and automatic operation. As an ordinary artisan will nonetheless readily appreciate, both parameters, i.e. the gas pressure and flow values, influence the setting of control values in accordance with a control algorithm. In one embodiment, if one of the two parameters reaches or exceeds its preset or pre-established maximum target value, a control element or actuator, as for example a valve, is caused to close. In another embodiment, operation of the control element is preferably influenced through a proportional/integral control process.

In accordance with the present invention, during automatic operation the automatic processing unit minimizes or reduces to zero the gas flow from an insufflation device when the pressure sensor recognizes a drop in pressure (which may, for example, be caused by opening of the tubes leading to the abdominal cavity) or detects no further rise in pressure. The automatic processing unit does not, however, differentiate a pressure reduction caused by gas leaking into the abdominal cavity or to the outside of the body of the patient through an instrument such, for example, as a hysteroscope. Thus, the cause of the leakage must be determined by the operator or examining physician on the basis of other criteria.

In a preferred embodiment of the control device, a pressure sensor and flow sensor are disposed so that the flow sensor is located downstream of the pressure sensor which, in turn, is located downstream of the control element (or actuator) such, for example, as a proportional solenoid valve. The flow sensor is positioned upstream of an insufflation instrument, as for example a probe or an endoscope channel, for feeding the gas into the body cavity.

In yet another embodiment constructed in accordance with the present invention, the control device digitally processes the measurement data from the pressure and flow sensors. Thus, if the pressure sensor generates a first analog direct-current value corresponding to the pressure in the conduit, the first analog value is converted to a corresponding first digital actual value by a first analog-to-digital converter preferably located in the control device. Similarly, if the flow sensor generates a second analog direct-current value corresponding to the gas flow rate in the conduit, the second analog value is converted to a corresponding second digital actual value by a second analog-to-digital converter also preferably positioned in the control device. The control device, on the basis of the digital first and second actual values and the pre-established target value, digitally processes the signals on the basis of a pre-selected control algorithm. A digital control value is computed and then supplied to a control element or actuator. Preferably, the control element is progressively or incrementally set by means of a pulse-duration modulated signal, which signal is converted from a digital control value and supplied to the control element. The control element may advantageously be a solenoid-controlled proportional valve.

To minimize and/or compensate for leakage of insufflated gas from the cavum uteri, the automatic processing unit implemented in the control device initially processes the first and second digital actual values and the pre-established target values and then communicates control values to the control element or actuator to reduce or return the intra-uterine pressure to a predetermined value at which the body cavity remains open and the tubes of the insufflation device are closed or no longer open. Through this progressively adjustable pressure regulation, the escape or leakage of insufflation medium is minimized and enhanced care in treatment of the patient is assured.

In one embodiment of the invention, the control device includes a microprocessor that arithmetically computes particular setting or control values from the measured pressure and flow values. In an alternative embodiment, the control device may have a microprocessor which stores at least one control algorithm as well as desired target values-in the form of characteristic tables. The microprocessor then carries out tabular processing based on the digitally-converted actual values of pressure and flow of the insufflated gas so as to determine the appropriate control values for the control element or actuator.

The microprocessor may interface with an input device that permits particular pressure and flow target values, within predetermined limits, to be variably input. A display device may also be connected to or associated with the microprocessor for displaying the measured or actual values and target values. It is further contemplated that the microprocessor be equipped with a hardware and software interface for connection to a conventional, commercially available personal computer so that the various functions and operations of the insufflation device, in accordance with the present invention, can be more flexibly implemented and controlled.

It is further contemplated that the automatic processing unit be implemented by an analog controller such, for example, as a PID (proportional/integral/derivative) controller.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

DETAILED DESCRIPTION OF THE DRAWINGS

In the drawings, wherein like reference characters denote similar elements throughout the several views.

DETAILED DESCRIPTION OF THE PRESENTLY PREFERRED EMBODIMENTS

Figure 1:
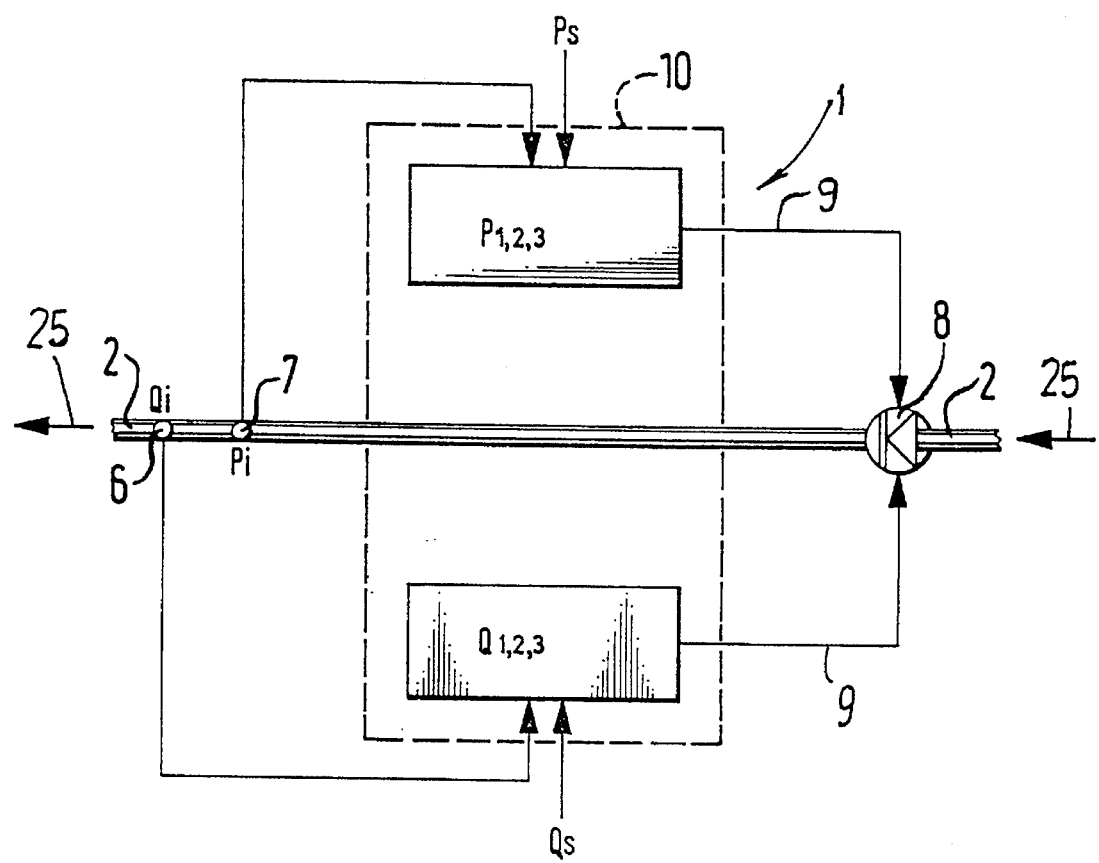
FIG. 1 is a semi-schematic drawing of a control device for an insufflation device in accordance with the present invention.

As shown in FIG. 1, a control device 1, constructed in accordance with the present invention, comprises an automatic processing unit 10, a gas flow sensor 6, pressure sensor 7, and control connections or links 9 operatively connecting the automatic processing unit 10 to a control element 8 that is interposed in a gas conduit 2 of an insufflation device. The gas flow sensor 6 and pressure sensor 7 are placed in the conduit 2, through which a gas medium for insufflation is guided in the direction indicated by the arrows 25 from a gas reservoir or supply (not shown) to a body cavity (not shown) of a patient. The gas flow sensor 6 and pressure sensor 7 measure the actual flow value $Q_i$ and actual pressure value $P_i$, respectively, in the conduit 2. The flow sensor 6 is preferably located downstream of the pressure sensor 7.

The values $P_i$, $Q_i$ are communicated to the automatic processing unit 10 of the control device 1 for processing using an integral/proportional control algorithm and preselectable pressure and flow target values $P_s$, and $Q_s$. The automatic processing unit 10 preferably includes separate control circuits for the respective generation of sequential control values $P_{1,2,3}$ and $Q_{1,2,3}$, which values are supplied to or used to operate the control element or actuator 8 located upstream of the sensor 6, 7 to regulate the downstream pressure in and/or flow of gas through the conduit 2. The control device 1 employs "feedback control" in that the regulation of pressure and flow in the conduit 2 by the automatic processing unit 10 is carried out as a function of the feedback of pressure and flow data collected by the sensors 7, 6 downstream of the control element 8.

Figure 2:
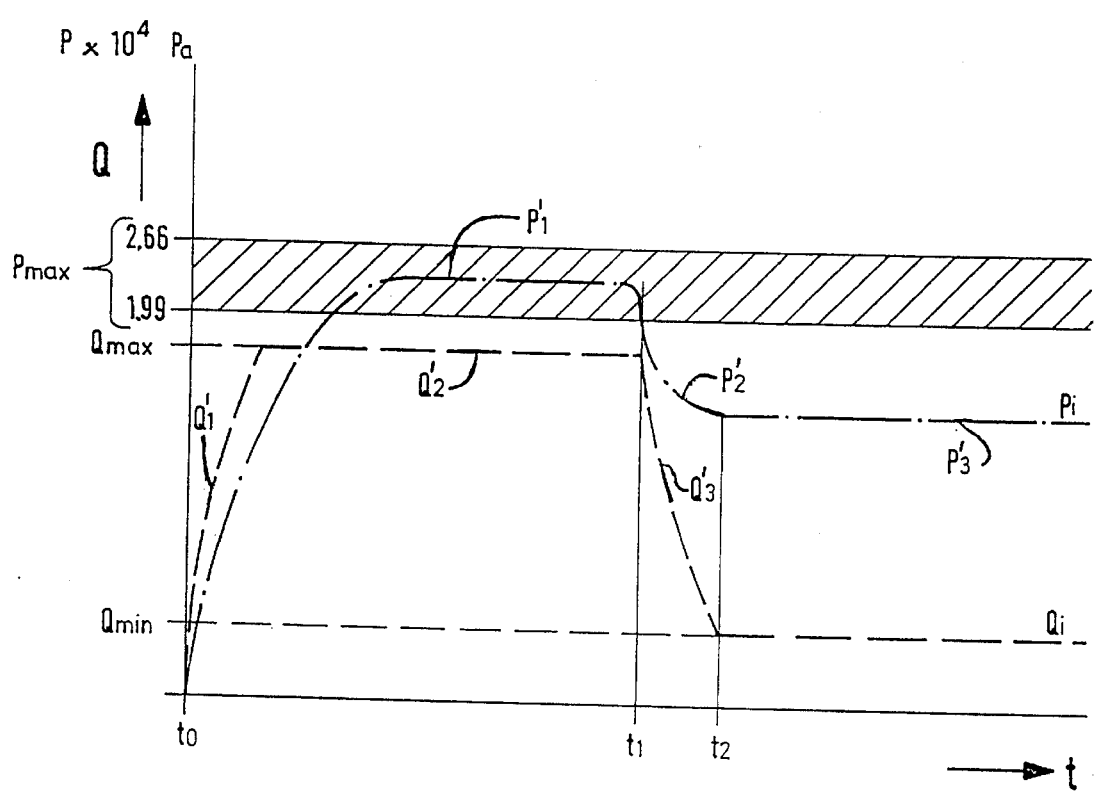
FIG. 2 is a representative plot of flow and pressure versus time, illustrating the functionality of the insufflation device of FIG. 1.

The functions, or variables, of an insufflation device pertinent to the present invention are illustrated in the function-time plot of FIG. 2. In FIG. 2, the pressure P and gas flow Q are shown on the ordinate, and time t is depicted on the abscissa. As represented by the shaded area, the intra-uterine pressure is not permitted to exceed a maximum pressure range of between about $1.99 \times 10^4$ and $2.66 \times 10^4$ Pa. The idealized curve of the measured pressure value $P_i$, as detected by the pressure sensor 7, is indicated by a dotted line. As seen in FIG. 2, that dotted line is subdivided into three branches: $P'_1$, $P'_2$ and $P'_3$. The idealized curve of the measured flow value $Q_i$, as detected by the flow sensor 6, is similarly indicated by a dashed line which is also subdivided into three branches, namely $Q'_1$, $Q'_2$ and $Q'_3$.

With continued reference to FIG. 2, and starting from a point in time $t_0$ at which the insufflation process is to begin, the gas flow $Q_1$ and pressure $P_i$ initially rise at a rapid rate. After a relatively short time, the gas flow $Q_i$ and pressure $P_1$ reach their respective maximum values $Q_{max}$ and $P_{max}$. The maximum pressure value $P_{max}$ lies in the shaded area between about $1.99 \times 10^4$ and $2.66 \times 10^4$ Pa. The maximum value $Q_{max}$ for the gas flow, on the other hand, is not permitted to exceed 100 ml/min. In accordance with the present invention, the control device 1 operates to ensure that the pressure $P_i$ and flow $Q_i$ in the conduit 2 do not exceed their respective maximum values $P_{max}$ and $Q_{max}$ (see branches P'$_1$ and Q'$_2$). If at any time $t_1$ there is a drop in pressure caused, by way of example, by the opening of tubes in a patient's body, then the automatic processing unit 10 will act to reduce the pressure $P_i$ from the highest pressure value (see branch P'$_1$) to a lower pressure value (see branch P'$_3$) until the measured gas flow $Q_i$ falls to zero (see branch Q'$_3$), or falls below a minimum value $Q_{min}$.

FIG. 2 further shows that at some time $t_2$ the ideal pressure and flow values begin to stabilize. After $t_2$, the pressure $P_i$ is kept constant (see branch P'$_3$) in order to allow the desired examinations or interventions to be carried out in the still open body cavity which remains in a reduced pressure state.

Figure 3:
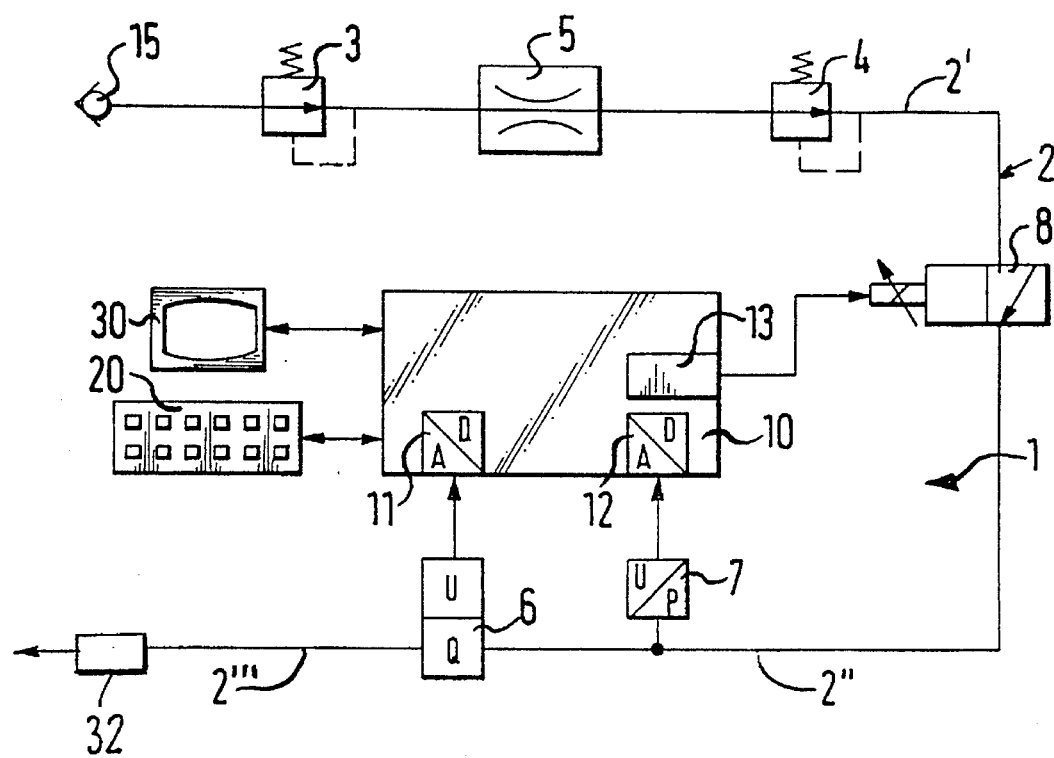
FIG. 3 is a semi-schematic diagram of a preferred embodiment of an insufflation device coupled to the control device of FIG. 1.

With reference now to FIG. 3, there is shown in enhanced detail a conduit 2 of an insufflation device coupled to a preferred embodiment of the control device 1. The conduit 2 has a first end into which gas is input and a second end from which gas is output and is subdivided into three portions 2', 2" and 2'''. Portion 2' serially connects a gas reservoir or supply 15 at the conduit first end to a first pressure reducer 3, then to a flow restrictor 5, and then to a second pressure reducer 4. Portion 2" connects the control element or actuator 8—here implemented by an operatively controllable proportional valve—to the second pressure reducer 4. Portion 2''' connects a pressure sensor 7 to the control valve 8. Within portion 2''', the flow sensor 6 is connected to the pressure sensor 7 downstream of the valve 8. Typically, during use, an operator connects an insufflation instrument 32 such, for example, as a probe or endoscope, to the portion 2'''.

In operation, the first pressure reducer 3 reduces the pressure of the gas from the gas reservoir or supply 15. The flow restrictor 5 operatively limits the maximum rate of gas flow from the reservoir 15. The second pressure reducer 4 then further limits the gas pressure in the conduit 2 to a maximum permissible level. The proportional valve 8 is controlled by the automatic processing unit 10, preferably implemented by a suitably programmed microprocessor, which receives feedback signals from the pressure sensor 7 and flow sensor 6. Based on the sensors' feedback and preestablished target pressure and flow values, the automatic processing unit 10 sends appropriate control values to the proportional valve 8 to selectively adjust the pressure and flow of gas through and out of the second or downstream end of the conduit 2.

The control device 1, and more particularly, the automatic processing unit 10, preferably includes or has associated with it a first analog-to-digital converter 11 which converts a direct current analog signal $U_p$ (corresponding to the actual flow value) produced by the flow sensor 6 into a corresponding digital signal. The control device 1 preferably also includes a second analog-to-digital converter which converts a direct current analog signal $U_p$ (corresponding to the actual pressure value) generated by the pressure sensor 7 into a corresponding digital value. It may further include a modulator 13 which generates a pulse-duration modulated control signal to the proportional valve 8 based on the first and second digital signals. The proportional valve 8 may, by way of example, be of the magnetic type. The automatic processing unit 10 may also include an interface to an input device 20 and to a display device 30 for respectively inputting and displaying various system parameters such, for example, as the target values for pressure and flow, the desired control algorithms, and appropriate time variables and control signals for starting and ending operation of the insufflation device. The visual display of data, particularly of the target and actual values for use in operating the control device 1, may advantageously be produced by the display device 30.

The basic signal processing of data or signals from the pressure 7 and flow 6 sensors in accordance with the invention will now be described in further detail.

Pressure Sensor

The actual pressure $P_i$ detected in portion 2' of the gas conduit 2 is converted by the pressure sensor 7 into, for example, an analog electrical current or voltage proportional to the actual pressure $P_i$, in the form:

$$U_p = P_i \times K_p$$

where $K_p$ may, for example, be a proportionality factor in Volts/Pa or Volts/mmHg or Volts/mbar, depending on the particular pressure sensor employed. From the analog voltage $U_p$, a digital actual value P'$_i$ is generated by the second analog-to-digital converter 12 and processed by the automatic processing unit 10. Using the digital actual value P'$_i$, the digital control variable $X_p$ is computed pursuant to the following equation:

$$X_p = [P_s - (P'_i - \text{Offset})] \times (\text{control constant})$$

where $P_s$ is the digital target pressure value, "offset" is a value dependent on the particular pressure sensor used, and the "control constant" is a value dependent on the particular processor, the programming language and the control element or actuator 8 that is employed to adjust the flow and pressure of gas in the conduit 2.

Flow Sensor

The flow sensor 6 produces in accordance with a voltage $U_Q$ related to the actual flow value $Q_i$ in accordance with the following equation:

$$U_Q = Q_i \times K_q$$

where $K_q$ is derived from the non-linear output curve of the particular flow sensor used and is itself dependent on $Q_i$.

From the voltage $U_Q$, the digital actual value Q'$_i$ is generated by the first analog-to-digital converter 11 and processed by the automatic processing unit 10. Thus, a digital control variable $X_Q$ for the control valve 8 is provided by the following equation:

$$X_Q = [Q_s - (Q'_i - \text{offset})] \times (\text{control constant})$$

where $Q_s$ is the digital target flow value, "offset" is a value dependent on the particular flow sensor used, and the "control constant" is dependent on the processor system, the programming language and the particular control element or actuator that is employed.

Depending on which of the setting or flow/pressure variables dominates, $X_p$ or $X_Q$ is converted into a corresponding pulse-duration modulated signal by the modulator 13 of or associated with the automatic processing unit 10, and the converted signal is supplied to the proportional valve 8. The control process for adjusting the valve 8 may preferably utilize a proportional/integral control method or algorithm.

During automatic operation—which may, for example, be initiated through the input device 20 (FIG. 3)—the control device is dynamically adjusted to cause the gas pressure and flow in the conduit 2 to behave as, in general, indicated in FIG. 2. The control device 1 detects any decrease in pressure in the conduit 2, regardless of its cause—as by the escape of gas into the abdominal cavity or through an insufflation instrument 32. On the other hand, during normal (i.e. non-automatic) operation, the control element or actuator such, for example, as the proportional valve 8 is caused to close or shut off if either the pressure or flow of gas exceeds its maximum pre-established limit value. In cases where values other than actual pressure and flow values are used, the control element or valve 8 may be regulated through a proportional/integral control process or algorithm.

In accordance with the present invention, therefore, a patient is not placed under unnecessary stress during insufflation when an operator activates the automatic operation mode of the insufflation device, since the control device 1 reduces the pressure in the body cavity of a patient when any decrease in pressure is detected—which often occurs during examination—while keeping the body cavity adequately open for examination.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

What is claimed is:

1. An apparatus for automatically insufflating a gas into a body cavity, comprising:

a conduit having an upstream first end for connection to a gas supply and a downstream second end for connection to an insufflation instrument and configured so that gas is fed from the gas supply, through said conduit and the insufflation instrument, and into the body cavity;

a selectively adjustable actuator located in and between said first and second ends of said conduit; and control means operable for automatically controlling a flow and pressure of the gas within said conduit by operatively adjusting said actuator, said control means including sensor means downstream of said actuator for detecting the gas flow and gas pressure in said conduit at a location upstream of the insufflation instrument and for outputting sensory signals related to the detected gas pressure and gas flow, and automatic processing means responsive to said sensory signals for operatively adjusting said actuator to reduce the pressure in the conduit until the detected flow of gas in said conduit downstream of the actuator approaches zero when the detected pressure drops or the detected pressure ceases to continue to increase.

2. The apparatus of claim 1, wherein said sensor means comprises:

a pressure sensor for detecting the gas pressure in said conduit at a first location downstream of said actuator; and a flow sensor for detecting the gas flow in said conduit at a second location downstream of said pressure sensor.

3. The apparatus of claim 2, wherein said pressure sensor is operative to generate a first analog signal value representing the detected gas pressure in the conduit, and wherein said control means further comprises first analog-to-digital converter means for receiving said first analog signal value and converting said first analog signal value to a corresponding first digital actual value.

4. The apparatus of claim 3, wherein said flow sensor is operative to generate a second analog signal value representing the detected gas flow in the conduit, and wherein said control means further comprises second analog-to-digital converter means for receiving said second analog signal value and converting said second analog signal value to a corresponding second digital actual value.

5. The apparatus of claim 4, wherein said automatic processing unit further comprises means for processing said first and second digital actual values in accordance with a pre-established control algorithm and pre-established target gas pressure and target gas flow values for generating therefrom first and second digital control values for use in adjusting said actuator.

6. The apparatus as claim 5, wherein said actuator comprises a solenoid-controlled valve, and wherein said control means further comprises pulse-duration modulation means for converting said first and second digital control values into a pulse-duration modulated signal for communication to said valve.

7. The apparatus of claim 4, wherein said automatic processing means further comprises a microprocessor operable for computing, from the first and second digital actual values and from a set of preselected target gas pressure and target gas flow values, a digital control value for use in operatively adjusting said actuator.

8. The apparatus of claim 4, wherein said automatic processing means further comprises storage means for storing at least one control algorithm and a table of target gas flow and gas pressure values, and a microprocessor connected to said storage means and operable for performing tabular processing using said algorithm and table values so as to calculate a digital control value for use in operatively adjusting said actuator.

9. The apparatus of claim 7, further comprising input means operatively connected to said microprocessor for inputting to the microprocessor the preselected target gas pressure and target gas flow values and the preselected gas pressure and gas flow limits.

10. The apparatus of claim 7, further comprising display means operatively connected to said microprocessor for visually displaying at least one of the detected gas pressure and gas flow signal values from said gas pressure and gas flow sensors and the target gas pressure and target gas flow values.

11. The apparatus of claim 1, wherein said automatic processing means comprises a microprocessor.

12. The apparatus of claim 11, wherein said microprocessor includes a hardware interface and a software interface for operative connection to a personal computer.

* * * * *